United States Patent [19]
Brookhart, III et al.

[11] Patent Number: 6,103,946
[45] Date of Patent: Aug. 15, 2000

[54] MANUFACTURE OF α-OLEFINS

[75] Inventors: Maurice S. Brookhart, III, Chapel Hill; Brooke L. Small, Carrboro, both of N.C.

[73] Assignees: E. I. du Pont de Nemours and Company, Wilmington, Del.; University of North Carolina, Chapel Hill, N.C.

[21] Appl. No.: 09/005,965

[22] Filed: Jan. 12, 1998

Related U.S. Application Data

[60] Provisional application No. 60/052,604, Jul. 15, 1997, and provisional application No. 60/065,538, Nov. 14, 1997.

[51] Int. Cl.$^7$ ................................................ C07C 2/02
[52] U.S. Cl. ......................... 585/523; 585/521; 585/522; 585/527
[58] Field of Search ..................... 585/511, 512, 585/513, 521, 522, 523, 527

[56] References Cited

U.S. PATENT DOCUMENTS

| | | | |
|---|---|---|---|
| 5,286,589 | 2/1994 | Go et al. | 430/58 |
| 5,955,555 | 9/1999 | Bennett | 526/133 |

FOREIGN PATENT DOCUMENTS

| | | |
|---|---|---|
| 89-045712 | 10/1989 | Japan . |
| 2-078663 | 3/1990 | Japan . |
| 10-007712 | 1/1998 | Japan . |
| WO 96/23010 | 8/1996 | WIPO . |
| WO 96/37523 | 11/1996 | WIPO . |
| WO 98/27124 | 6/1998 | WIPO . |
| WO 98/30612 | 7/1998 | WIPO . |

OTHER PUBLICATIONS

L. Sacconi, et al., High–spin Five–co–ordinate Nickel(II) and Cobalt(II) Complexes with 2,6–Diacetylpyridinebis(imines), *J. Chem. Soc.*, A, 1510–1515, 1968.

Paul E. Figgins, et al., Complexes of Iron (II), Cobalt(II) and Nickel(II) with Biacetyl–bis–methylimine, 2–Pyridinal–m-ethylimine and 2,6–Pyridindial–bis–methylimine, *J. Am. Chem. Soc.*, 82, 820–824, Feb. 20, 1960.

Thomas W. Bell, et al., Molecular Architecture. 1. Sodium, Potassium, and Strontium Complexes of a Hexaazamacrocycle, an 18–Crown–6/Torand Analogue, *J. Am. Chem. Soc.*, 113, 3115–3122, 1991.

Francis Lions, et al., Tridentate Chelate Compounds. I, *J. Am. Chem. Soc.*, 79, 2733–2738, Jun. 5, 1957.

PCT/US97/23556 International Search Report dated May 13, 1998.

Reinhard Nesper, et al., Palladium (II) complexes of chiral tridentate nitrogen pybox ligands, *Journal of Organometallic Chemistry*, vol. 1, No. 507, 85–101, 1996.

PCT/US98/14306 PCT International Search Report dated Oct. 12, 1998.

*Primary Examiner*—Marian C. Knode
*Assistant Examiner*—Thuan D. Dang
*Attorney, Agent, or Firm*—Joel D. Citron; Craig H. Evans; Bart E. Lerman

[57] ABSTRACT

Alpha-olefins are manufactured in high yield and with very high selectivity by contacting ethylene with an iron complex of a selected 2,6-pyridinedicarboxaldehyde bisimine or a selected 2,6-diacylpyridine bisimine, and in some cases a selected activator compound such as an alkyl aluminum compound. Novel bisimines and their iron complexes are also disclosed. The α-olefins are useful as monomers and chemical intermediates.

41 Claims, No Drawings

MANUFACTURE OF α-OLEFINS

This application claims the benefit of U.S. Provisional Application Ser. No. 60/052,604, filed Jul. 15, 1997 and of U.S. Provisional Application Ser. No. 60/065,538, filed Nov. 14, 1997.

FIELD OF THE INVENTION

Alpha-olefins may be manufactured in high yield and with very high selectivity by contacting ethylene with an iron complex of a selected 2,6-pyridinedicarboxaldehyde bisimine or a selected 2,6-diacylpyridine bisimine, and usually a selected activator compound.

TECHNICAL BACKGROUND

Alpha-olefins, especially those containing about 6 to about 20 carbon atoms, are important items of commerce, with about 1.5 million tons reportedly being produced in 1992. The α-olefins are used as intermediates in the manufacture of detergents, as monomers (especially in linear low density polyethylene), and as intermediates for many other types of products. As a consequence, improved methods of making these compounds are of interest.

Most commercially produced α-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as $AlCl_3$. In all of these processes significant amounts of branched and/or internal olefins and/or diolefins, are produced. Since in most instances these are undesired, and often difficult to separate from the desired linear α-olefins, minimization of these byproducts is sought.

SUMMARY OF THE INVENTION

This invention concerns a first process for the production of α-olefins, comprising, contacting, at a temperature of about −100° C. to about +300° C., a compound of the formula

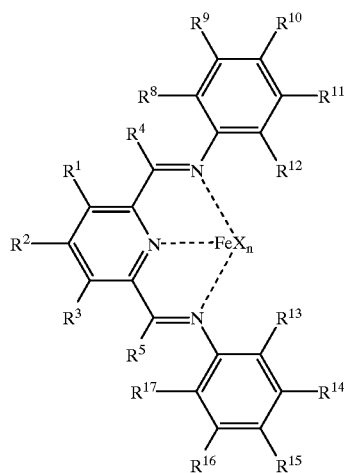

(I)

with ethylene and:

(a) a first compound W, which is a neutral Lewis acid capable of abstracting $X^-$ an alkyl group or a hydride group from Fe to form $WX^-$, $(WR^{20})^-$ or $WH^-$ and which is also capable of transferring an alkyl group or a hydride to Fe, provided that $WX^-$ is a weakly coordinating anion; or (b) a combination of second compound which is capable of transferring an alkyl or hydride group to Fe and a third compound which is a neutral Lewis acid which is capable of abstracting $X^-$, a hydride or an alkyl group from Fe to form a weakly coordinating anion;

wherein:

each X is an anion;

n is 1, 2 or 3 so that the total number of negative charges on said anion or anions is equal to the oxidation state of an Fe atom present in (I);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^9$, $R^{10}$, $R^{11}$, $R^{14}$, $R^{15}$ and $R^{16}$ are each independently hydrogen, hydrocarbyl, an inert functional group or substituted hydrocarbyl;

$R^8$ is a primary carbon group, a secondary carbon group or a tertiary carbon group; and $R^{20}$ is alkyl;

and provided that:

when $R^8$ is a primary carbon group none, one or two of $R^{12}$, $R^{13}$ and $R^{17}$ are primary carbon groups, and the remainder of $R^{12}$, $R^{13}$ and $R^{17}$ are hydrogen;

when $R^8$ is a secondary carbon group, none or one of $R^{12}$, $R^{13}$ and $R^{17}$ is a primary carbon group or a secondary carbon group and the remainder of $R^{12}$, $R^{13}$, and $R^{17}$ are hydrogen;

when $R^8$ is a tertiary carbon group all of $R^{12}$, $R^{13}$ and $R^{14}$ are hydrogen; and any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

Also disclosed herein is a compound of the formula

This invention includes a compound of the formula

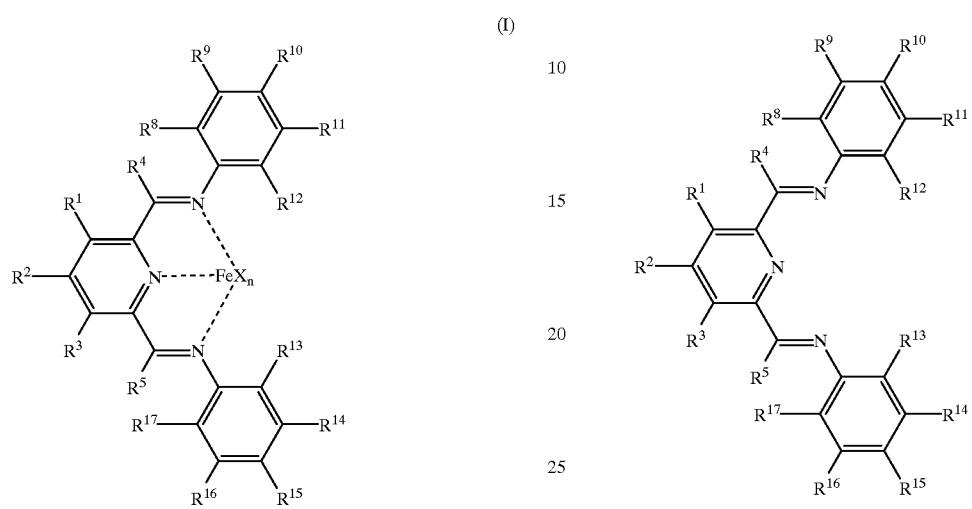

wherein:

each X is an anion;

n is 1, 2 or 3 so that the total number of negative charges on said anion or anions is equal to the oxidation sate of a Fe atom present in (I);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl; and $R^9$, $R^{10}$, $R^{11}$, $R^{14}$, $R^{15}$ and $R^{16}$ are each independently hydrogen, hydrocarbyl, an inert functional group or substituted hydrocarbyl; $R^8$ is a primary carbon group, a secondary carbon group or a tertiary carbon group;

and provided that:

when $R^8$ is a primary carbon group none, one or two of $R^{12}$, $R^{13}$ and $R^{17}$ are primary carbon groups, and the remainder of $R^{12}$, $R^{13}$ and $R^{17}$ are hydrogen;

when $R^8$ is a secondary carbon group, none or one of $R^{12}$, $R^{13}$ and $R^{17}$ is a primary carbon group or a secondary carbon group and the remainder of $R^{12}$, $R^{13}$, and $R^{17}$ are hydrogen; and when $R^8$ is a tertiary carbon group all of $R^{12}$, $R^{13}$ and $R^{14}$ are hydrogen; any two of $R^8$, $R^9$, $R^{10}$, $R^{11}$, $R^{12}$, $R^{13}$, $R^{14}$, $R^{15}$, $R^{16}$ and $R^{71}$ vicinal to one another, taken together may form a ring.

wherein:

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl; and $R^9$, $R^{10}$, $R^{11}$, $R^{14}$, $R^{15}$ and $R^{16}$ are each independently hydrogen, hydrocarbyl, an inert functional group or substituted hydrocarbyl; $R^8$ is a primary carbon group, a secondary carbon group or a tertiary carbon group;

and provided that:

when $R^8$ is a primary carbon group none, one or two of $R^{12}$, $R^{13}$ and $R^{17}$ are primary carbon groups, and the remainder of $R^{12}$, $R^{13}$ and $R^{17}$ are hydrogen;

when $R^8$ is a secondary carbon group, none or one of $R^{12}$, $R^{13}$ and $R^{17}$ is a primary carbon group or a secondary carbon group and the remainder of $R^{12}$, $R^{13}$, and $R^{17}$ are hydrogen;

when $R^8$ is a tertiary carbon group all of $R^{12}$, $R^{13}$ and $R^{14}$ are hydrogen; and any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

This invention also concerns a second process for the production of α-olefins, comprising contacting, at a temperature of about −100° C. to about +300° C., a Fe[II] or Fe[III] complex of a tridentate ligand of the formula

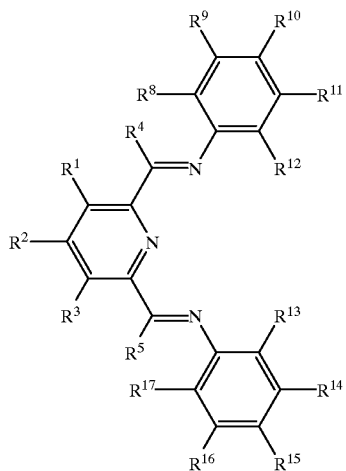

(II)

with ethylene, wherein:

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^9$, $R^{10}$, $R^{11}$, $R^{14}$, $R^{15}$ and $R^{16}$ are each independently hydrogen, hydrocarbyl, an inert functional group or substituted hydrocarbyl;

$R^8$ is a primary carbon group, a secondary carbon group or a tertiary carbon group;

and provided that:

when $R^8$ is a primary carbon group none, one or two of $R^{12}$, $R^{13}$ and $R^{17}$ are primary carbon groups, and the remainder of $R^{12}$, $R^{13}$ and $R^{17}$ are hydrogen;

when $R^8$ is a secondary carbon group, none or one of $R^{12}$, $R^{13}$ and $R^{14}$ is a primary carbon group or a secondary carbon group and the remainder of $R^{12}$, $R^{13}$, and $R^{17}$ are hydrogen;

when $R^8$ is a tertiary carbon group all of $R^{12}$, $R^{13}$ and $R^{14}$ are hydrogen;

any two of $R^8, R^9, R^{10}, R^{11}, R^{12}, R^{13}, R^{14}, R^{15}, R^{16}$ and $R^{17}$ vicinal to one another, taken together may form a ring;

an Fe[II] or Fe[III] atom also has bonded to it an empty coordination site or a ligand that may be displaced by said ethylene, and a ligand that may add to said ethylene.

This invention also includes a compound of the formula

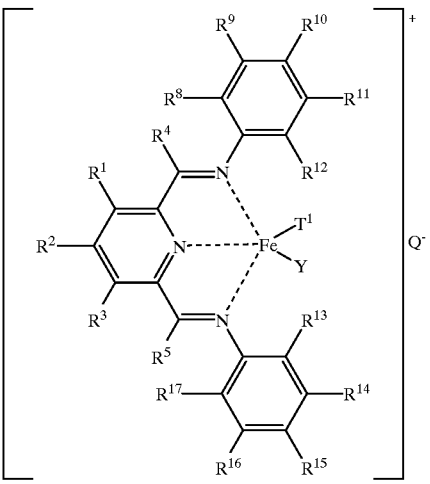

(IV)

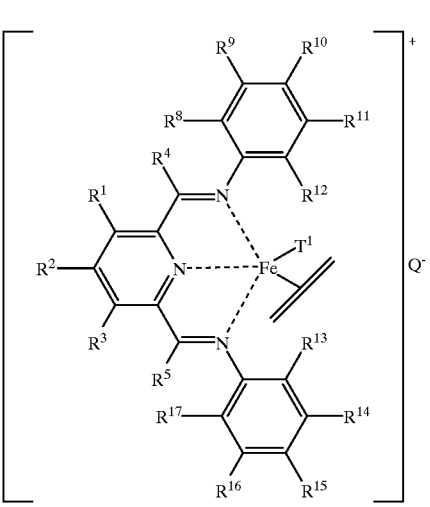

(V)

or

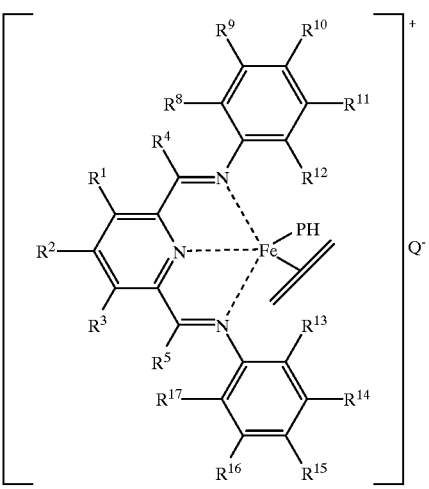

(VI)

wherein:

R$^1$, R$^2$ and R$^3$ are each independently hydrogen, hydrocarbyl, substituted hydrocarbyl, or an inert functional group;

R$^4$ and R$^5$ are each independently hydrogen, hydrocarbyl, an inert functional group or substituted hydrocarbyl, R$^9$, R$^{10}$, R$^{11}$, R$^{14}$, R$^{15}$ and R$^{16}$ are each independently hydrogen, hydrocarbyl, an inert functional group or substituted hydrocarbyl;

R$^8$ is a primary carbon group, a secondary carbon group or a tertiary carbon group;

T$^1$ is hydride or alkyl or any other anionic ligand into which ethylene can insert;

Y is a vacant coordination site, or neutral ligand capable of being displaced by ethylene;

Q is a relatively non-coordinating anion; and

P is a divalent (poly)ethylene group of the formula —(CH$_2$CH$_2$)$_x$— wherein x is an integer of 1 or more;

and provided that:

when R$^8$ is a primary carbon group none, one or two of R$^{12}$, R$^{13}$ and R$^{17}$ are primary carbon groups, and the remainder of R$^{12}$, R$^{13}$ and R$^{17}$ are hydrogen;

when R$^8$ is a secondary carbon group, none or one of R$^{12}$, R$^{13}$ and R$^{17}$ is a primary carbon group or a secondary carbon group and the remainder of R$^{12}$, R$^{13}$, and R$^{17}$ are hydrogen;

when R$^8$ is a tertiary carbon group all of R$^{12}$, R$^{13}$ and R$^{14}$ are hydrogen; and any two of R$^8$, R$^9$, R$^{10}$, R$^{11}$, R$^{12}$, R$^{13}$, R$^{14}$, R$^{15}$, R$^{16}$ and R$^{17}$ vicinal to one another, taken together may form a ring.

This invention also concerns a third process for the production of α-olefins, comprising, contacting, at a temperature of about −100° C. to about +300° C., ethylene and a compound of the formula

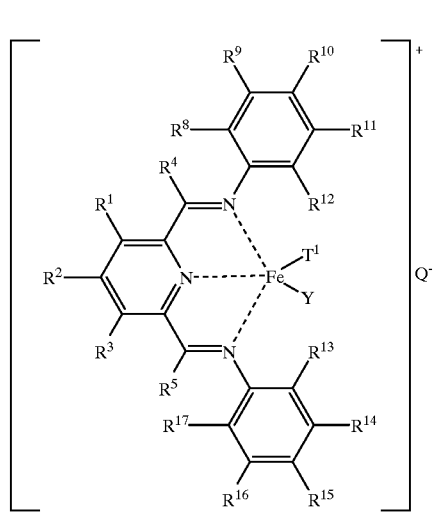

(IV)

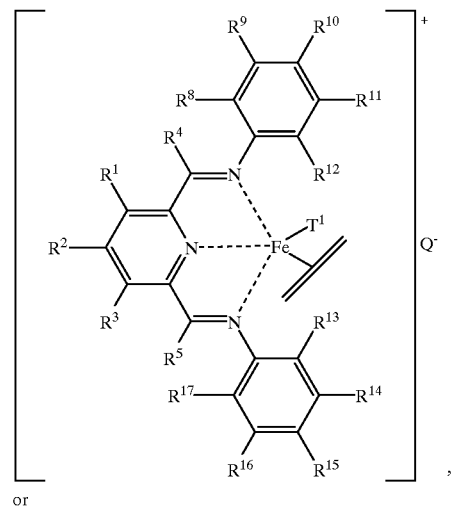

(V)

or

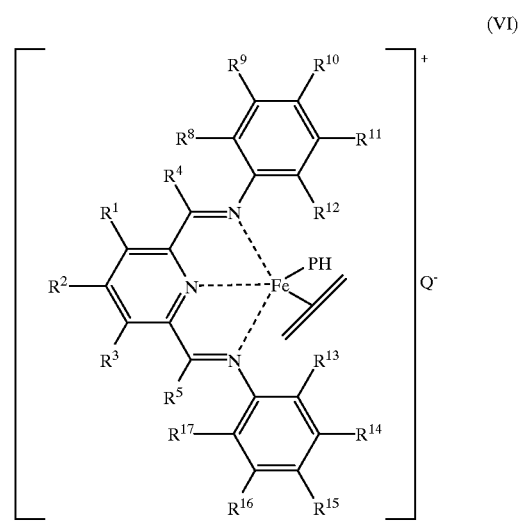

(VI)

wherein:

R$^1$, R$^2$ and R$^3$ are each independently hydrogen, hydrocarbyl, substituted hydrocarbyl, or an inert functional group;

R$^4$ and R$^5$ are each independently hydrogen, hydrocarbyl, an inert functional group or substituted hydrocarbyl, R$^9$, R$^{10}$, R$^{11}$, R$^{14}$, R$^{15}$ and R$^{16}$ are each independently hydrogen, hydrocarbyl, an inert functional group or substituted hydrocarbyl;

R$^8$ is a primary carbon group, a secondary carbon group or a tertiary carbon group;

T$^1$ is hydride or alkyl or any other anionic ligand into which ethylene can insert;

Y is a vacant coordination site, or a neutral ligand capable of being displaced by ethylene;

Q is a relatively non-coordinating anion; and

P is a divalent (poly)ethylene group of the formula —(CH$_2$CH$_2$)$_x$— wherein x is an integer of 1 or more;

and provided that:

when R$^8$ is a primary carbon group none, one or two of R$^{12}$, R$^{13}$ and R$^{17}$ are primary carbon groups, and the remainder of R$^{12}$, R$^{13}$ and R$^{17}$ are hydrogen;

when $R^8$ is a secondary carbon group, none or one of $R^{12}$, $R^{13}$ and $R^{17}$ is a primary carbon group or a secondary carbon group and the remainder of $R^{12}$, $R^{13}$, and $R^{17}$ are hydrogen;

when $R^8$ is a tertiary carbon group all of $R^{12}$, $R^{13}$ and $R^{14}$ are hydrogen; and any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

DETAILS OF THE INVENTION

Herein, certain terms are used. Some of them are:

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^{18}$ wherein $R^{18}$ is hydrocarbyl or substituted hydrocarbyl. In cases in which the functional group may be near an iron atom, such as $R^4$, $R^5$, $R^8$, $R^{12}$, $R^{13}$, and $R^{17}$ the functional group should not coordinate to the iron atom more strongly than the groups in compounds containing $R^4$, $R^5$, $R^8$, $R^{12}$, $R^{13}$ and $R^{17}$ which are shown as coordinating to the iron atom, that is they should not displace the desired coordinating group.

By an "alkyl aluminum compound" is meant a compound in which at least one alkyl group is bound to an aluminum atom. Other groups such as alkoxide, oxygen, and halogen may also be bound to aluminum atoms in the compound. See below for preferred alkylaluminum compounds.

By "neutral Lewis base" is meant a compound, which is not an ion, which can act as a Lewis base. Examples of such compounds include ethers, amines, sulfides, and organic nitrites.

By "cationic Lewis acid" is meant a cation which can act as a Lewis acid. Examples of such cations are sodium and silver cations.

By relatively noncoordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Strauss, Chem. Rev., vol. 93, p. 927–942 (1993), both of which are hereby included by reference. Among such anions are those formed from alkylaluminum compounds, defined above, and $X^-$, including $R^9{}_3AlX^-$, $R^9{}_2AlClX^-$, $R^9AlCl_2X^-$, and "$R^9AlOX^-$". Other useful noncoordinating anions include $BAF^-$ {BAF=tetrakis[3,5-bis(trifluoromethyl)phenyl]borate}, $SbF_6^-$, $PF_6^-$, and $BF_4^-$, trifluoromethanesulfonate, p-toluenesulfonate, $(R_fSO_2)_2N^-$ (wherein $R_f$ is perfluoroalkyl), and $(C_6F_5)_4B^-$.

By formation of an α-olefin is meant formation of a compound (or mixture of compounds) of the formula $H(CH_2CH_2)_qCH{=}CH_2$ wherein q is an integer of 1 to about 18. In most such reactions, a mixture of compounds will result which have differing values of q, and in most reactions to form the α-olefins some of the α-olefins formed will have q values of more than 18. Preferably less than 50 weight percent, more preferably less than 20 weight percent of the product mixture will have q values over 18. The product mixture may contain small amounts (preferably less than 30 weight percent, more preferably less than 10 weight percent, and especially preferably less than 2 weight percent) of other types of compounds such as alkanes, branched alkenes, dienes, and/or internal olefins.

By an empty coordination site is meant a potential coordination site that does not have a ligand bound to it. Thus if an ethylene molecule is in the proximity of the empty coordination site, the ethylene molecule may coordinate to the metal atom.

By a "primary carbon group" herein is meant a group of the formula —$CH_2$—, wherein the free valence—is to any other atom (the bond represented by the hyphen is to the benzene ring to which the primary carbon group is attached). Thus the free valence—may be bonded to a hydrogen atom, halogen atom, a carbon atom, an oxygen atom, a sulfur atom, etc. In other words, the free valence—may be to hydrogen, hydrocarbyl, substituted hydrocarbyl or a functional group. Examples of primary carbon groups include —$CH_3$, —$CH_2CH(CH_3)_2$, —$CH_2Cl$, —$CH_2C_6H_5$, —$OCH_3$ and —$CH_2OCH_3$.

By a secondary carbon group is meant the group

wherein both free bonds represented by the dashed lines are to an atom or atoms other than hydrogen. These atoms or groups may be the same or different. In other words the free valences represented by the dashed lines may be hydrocarbyl, substituted hydrocarbyl or functional groups. Examples of secondary carbon groups include —$CH(CH_3)_2$, —$CHCl_2$, —$CH(C_6H_5)_2$, cyclohexyl, —$CH(CH_3)OCH_3$, and —$CH{=}CCH_3$.

By a "tertiary carbon group" is meant a group of the formula

wherein the solid line is the bond to the benzene ring and the three free bonds represented by the dashed lines are to an atom or atoms other than hydrogen. In other words, the bonds represented by the dashed lines are to hydrocarbyl, substituted hydrocarbyl or inert functional groups. Examples of tetiary carbon groups include —C(CH$_3$)$_3$, —C(C$_6$H$_5$)$_3$, —CCl$_3$, —C(CH$_3$)$_2$OCH$_3$, —C≡CH, —C(CH$_3$)CH=CH$_2$, and 1-adamantyl.

By a ligand that may add to ethylene is meant a ligand coordinated to a metal atom into which an ethylene molecule (or a coordinated ethylene molecule) may insert to start or continue an oligomerization. For instance, this may take the form of the reaction (wherein L is a ligand):

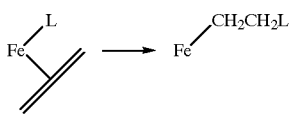

Note the similarity of the structure on the left-hand side of this equation to compounds (V) and (VI) (see below).

Compounds useful as ligands are diimines of 2,6-pyridinedicarboxaldehyde or 2,6-diacylpyridines of the general formula

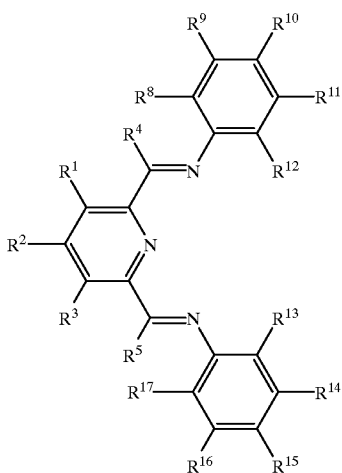

(II)

wherein all of the "R" groups are as defined above. In preferred compounds (I) and (II), and all other preferred compounds in which the following "R" groups appear:

R$^4$ and R$^5$ are methyl or hydrogen; and/or

R$^1$, R$^2$, and R$^3$ are all hydrogen; and/or

R$^9$, R$^{10}$, R$^{11}$, R$^{14}$, R$^{15}$ and R$^{16}$ are all hydrogen; and/or R$^{12}$ and R$^{17}$ are each independently methyl, ethyl, propyl or isopropyl, more preferably both are methyl or ethyl; and/or each X is a monovalent anion, more preferably selected from the group consisting of halide and nitrile.

It is also preferred that in all compounds in which they appear:

if R$^8$ is a primary carbon group, R$^{13}$ is a primary carbon group and R$^{12}$ and R$^{17}$ are hydrogen;

if R$^8$ is a secondary carbon group, R$^{13}$ is a primary or secondary carbon group, more preferably a secondary carbon group, and R$^{12}$ and R$^{17}$ are hydrogen.

In all specific preferred compounds in which they appear it is preferred that:

R$^4$ and R$^5$ are methyl, R$^9$, R$^{10}$, R$^{11}$, R$^{14}$, R$^{15}$ and R$^{16}$ are all hydrogen, and R$^{12}$ and R$^{17}$ are both methyl;

R$^4$ and R$^5$ are methyl, R$^9$, R$^{10}$, R$^{11}$, R$^{14}$, R$^{15}$ and R$^{16}$ are all hydrogen, and R$^{12}$ and R$^{17}$ are both ethyl;

R$^4$ and R$^5$ are methyl, R$^9$, R$^{10}$, R$^{14}$, R$^{15}$ and R$^{16}$ are all hydrogen, and R$^{12}$ and R$^{17}$ are both isopropyl;

R$^4$ and R$^5$ are methyl, R$^9$, R$^{10}$, R$^{11}$, R$^{14}$, R$^{15}$ and R$^{16}$ are all hydrogen, and R$^{12}$ and R$^{17}$ are both n-propyl;

R$^4$ and R$^5$ are methyl, R$^9$, R$^{10}$, R$^{11}$, R$^{14}$, R$^{15}$ and R$^{16}$ are all hydrogen, and R$^{12}$ and 17are both chloro; and R$^4$ and R$^5$ are methyl, R$^9$, R$^{10}$, R$^{11}$, R$^{14}$, R$^{15}$ and R$^{16}$ are all hydrogen, and R$^{12}$ and R$^{17}$ are both trifluoromethyl.

In all of the above specific compounds it is preferred that X is selected from the group consisting of chloride, bromide and nitrate, and more preferably that it is chloride.

Compounds such as (II) and may be made by the reaction of a compound of the formula

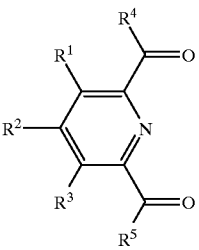

(III)

with a compound of the formula H$_2$NR$^6$ or H$_2$NR$^7$, wherein R$^6$ and R$^7$ are as described above. These reactions are often catalyzed by carboxylic acids, such as formic acid. Reactions such as these are described in Examples 1–3.

The iron complexes may be formed by reacting the appropriate tridentate ligand with an iron salt such as an iron halide or a compound such as iron [III] nitrate. See Examples 4–6 for preparation of iron complexes.

In the first oligomerization process (to produce α-olefins) described herein an iron complex (I) is contacted with ethylene and a neutral Lewis acid W capable of abstracting X$^-$, hydride or alkyl (R$^{20}$) from (I) to form a weakly coordinating anion, and must alkylate or be capable of adding a hydride ion to the iron atom, or an additional alkylating agent or an agent capable of adding a hydride anion to the iron atom must be present. The neutral Lewis acid is originally uncharged (i.e., not ionic). Suitable neutral Lewis acids include SbF$_5$, Ar$_3$B (wherein Ar is aryl), and BF$_3$. Suitable cationic Lewis acids or Bronsted acids include NaBAF, silver trifluoromethanesulfonate, HBF$_4$, or [C$_6$H$_5$NH(CH$_3$)$_2$]$^+$[B(C$_6$F$_5$)$_4$]$^-$. In those instances in which (I) (and similar catalysts which require the presence of a neutral Lewis acid or a cationic Lewis or Bronsted acid), does not contain an alkyl or hydride group already bonded to the iron atom, the neutral Lewis acid or a cationic Lewis or Bronsted acid also alkylates or adds a hydride to the iron or a separate alkylating or hydriding agent is present, i.e., causes an alkyl group ($R^{20}$) or hydride to become bonded to the iron atom.

It is preferred that $R^{20}$ contains 1 to 4 carbon atoms, and more preferred that $R^{20}$ is methyl or ethyl.

For instance, alkyl aluminum compounds (see next paragraph) may alkylate (I). However, not all alkylaluminum compounds may be strong enough Lewis acids to abstract $X^-$ or an alkyl group from the iron atom. In that case a separate Lewis acid strong enough to do the abstraction must be present. For instance, $(C_6F_5)_3B$ or $(C_6H_5)_3B$ are useful Lewis acids, and could be used in combination with, for example, an alkylaluminum compound such as triethylaluminum.

A preferred neutral Lewis acid, which can alkylate the iron, is a selected alkyl aluminum compound, such as $R^{19}{}_3Al$, $R^{19}AlCl_2$, $R^{19}{}_2AlCl_2$, and "$R^{19}AlO$" (alkylaluminoxanes), wherein $R^{19}$ is alkyl containing 1 to 25 carbon atoms, preferably 1 to 4 carbon atoms. Suitable alkyl aluminum compounds include methylaluminoxanes (which are oligomers with the general formula $[MeAlO]_n$), $(C_2H_5)_2AlCl$, $C_2H_5AlCl_2$, and $[(CH_3)_2CHCH_2]_3Al$.

Metal hydrides such as $NaBH_4$ may be used to bond hydride groups to the Fe.

In the second oligomerization process described herein an iron complex of (II) is either added to the oligomerization process or formed in situ in the process. In fact, more than one such complex may be formed during the course of the process, for instance formation of an initial complex and then reaction of that complex to form an active ended oligomer containing such a complex.

Examples of such complexes which may be formed initially in situ include

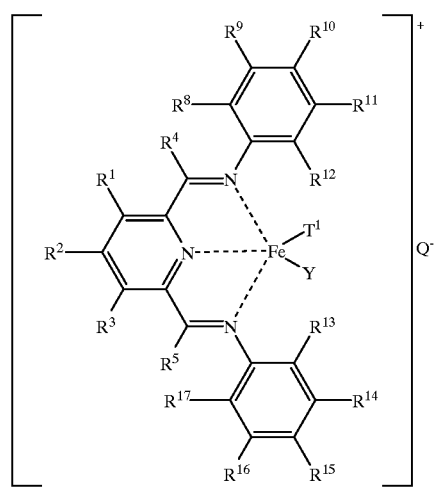

(IV)

and

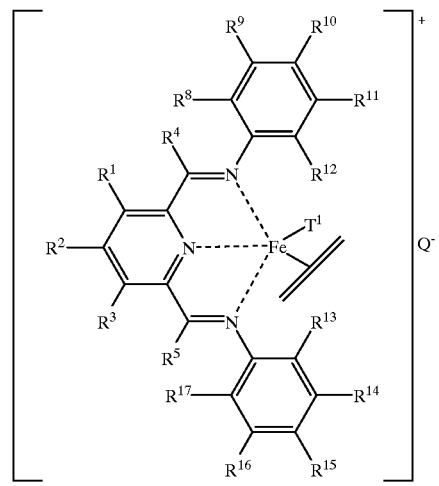

(V)

and
wherein the "R" substituents are as defined above, $T^1$ is hydride or alkyl or any other anionic ligand into which ethylene can insert, Y is a vacant coordination site, or a neutral ligand capable of being displaced by ethylene, and Q is a relatively non-coordinating anion. Complexes may be added directly to the process or formed in situ. For instance, (IV) may be formed by the reaction of (I) with a neutral Lewis acid such as an alkyl aluminum compound. Another method of forming such a complex in situ is combining a suitable iron compound such iron chloride, (II) and an alkyl aluminum compound. Other iron salts in which anions similar to chloride are present, and which may be removed by reaction with the Lewis or Bronsted acid. For instance iron halides, nitrates and carboxylates (such as acetates) may be used, particularly if they are slightly soluble in the process medium. It is preferred that these precursor iron salts be at least somewhat soluble in the process medium.

After the ethylene oligomerization has started, the complex may be in a form such as

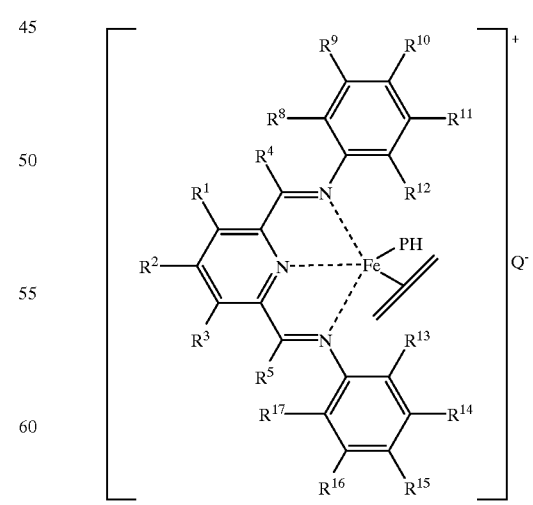

(VI)

wherein, as before, the "R" substituents and Q are as defined above, and P is a divalent (oligo)ethylene group of the formula —$(CH_2CH_2)_x$— wherein x is an integer of 1 or more. The "end group" on P in this instance is written as H, since as the oligomerization proceeds to form α-olefins, the end group must of necessity be H. It could at some time, especially at the beginning of the oligomerization, be $T^1$. It is preferred that Fe be in +2 oxidation state in (I), (IV), (V) and (VI).

Compounds such as (IV), (V) and (VI) may or may not be stable away from an environment similar to that of the oligomerization process.

(IV), (V) and (VI) may also be used, in the absence of any "co-catalysts" or "activators" to oligomerize ethylene in a third oligomerization process. Except for the ingredients in the process, the process conditions for the third process, such as temperature, pressure, oligomerization medium, etc., may be the same as for the first and second oligomerization processes, and preferred conditions for those processes are also preferred for the third oligomerization process.

In all the oligomerization processes herein, the temperature at which it is carried out is about −100° C. to about +300° C., preferably about 0° C. to about 200° C., more preferably about 50° C. to about 150° C. It is preferred to carry out the oligomerization under ethylene (gauge) pressures from about 0 kPa to about 35 MPa, more preferably about 500 kPa to about 15 MPa. It is preferred that the oligomerization be carried under conditions at which the reaction is not significantly diffusion limited.

The oligomerization processes herein may be run in the presence of various liquids, particularly aprotic organic liquids. The catalyst system, ethylene, and α-olefin product may be soluble or insoluble in these liquids, but obviously these liquids should not prevent the oligomerization from occurring. Suitable liquids include alkanes, alkenes cycloalkanes, selected halogenated hydrocarbons, and aromatic hydrocarbons. Specific useful solvents include hexane, toluene, the α-olefins themselves, and benzene.

The formation of the α-olefins as described herein is relatively rapid in many instances, and significant yields can be obtained in less than an hour. Under the correct conditions very high selectivity for an α-olefin is shown, see for instance Examples 8–17.

Also under the correct conditions mixtures of α-olefins containing desirable numbers of carbon atoms are obtained. A measure of the molecular weights of the olefins obtained is factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276. This is defined as:

$$K=n(C_{n+2} \text{ olefin})/n(C_n \text{ olefin})$$

wherein $n(C_n$ olefin) is the number of moles of olefin containing n carbon atoms, and $n(C_{n+2}$ olefin) is the number of moles of olefin containing n+2 carbon atoms, or in other words the next higher oligomer of $C_n$ olefin. From this can be determined the weight (mass) fractions of the various olefins in the resulting oligomeric reaction product mixture.

The K factor is preferred to be in the range of about 0.7 to about 0.8 to make the α-olefins of the most commercial interest. It is also important to be able to vary this factor, so as to produce those olefins which are in demand at the moment. Examples 8 to 17 show that this can be done in the present oligomerization processes.

The α-olefins made herein may be further polymerized with other olefins to form polyolefins, especially linear low density polyethylenes, which are copolymers containing ethylene. They may also be homopolymerized. These polymers may be made by a number of known methods, such as Ziegler-Natta-type polymerization, metallocene catalyzed polymerization, and other methods, see for instance World Patent Application 96/23010, see for instance Angew. Chem., Int. Ed. Engl., vol. 34, p. 1143–1170 (1995), European Patent Application 416,815 and U.S. Pat. No. 5,198, 401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, p. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylenes, and all of these are hereby included by reference.

The α-olefins made herein may be converted to alcohols by known processes, these alcohols being useful for a variety of applications such as intermediates for detergents or plasticizers. The α-olefins may be converted to alcohols by a variety of processes, such as the oxo process followed by hydrogenation, or by a modified single step oxo process (the 'modified Shell process'), see for instance B. Elvers, et al., Ed., Ullmann's Encyclopedia of Chemical Technology, $5^{th}$ Ed., Vol. A18, VCH Verlagsgesellschaft mbH, Weinheim, 1991, p. 321–327, which is hereby included by reference.

The ethylene oligomerizations herein may also initially be carried out in the solid state by, for instance, supporting and active catalyst or catalyst precursor on a substrate such as silica or alumina. If a catalyst precursor, such as an iron halide or nitrate, it may be activated with a Lewis (such as W, for instance an alkylaluminum compound) and exposing it to ethylene. Alternatively a solution of the catalyst precursor may be exposed to a support having an alkylaluminum compound on its surface. The support may also be able to take the place of the Lewis or Bronsted acid, for instance an acidic clay such as montmorillonite. Another method of making a supported catalyst is to start a polymerization or at least make an iron complex of another olefin or oligomer of an olefin such as cyclopentene on a support such as silica or alumina. All of these "heterogeneous" catalysts may be used to catalyze oligomerization in the gas phase or the liquid phase. By gas phase is meant that the ethylene is transported to contact with the catalyst particle while the ethylene is in the gas phase.

Some of the compounds made or used in the Examples are shown below:

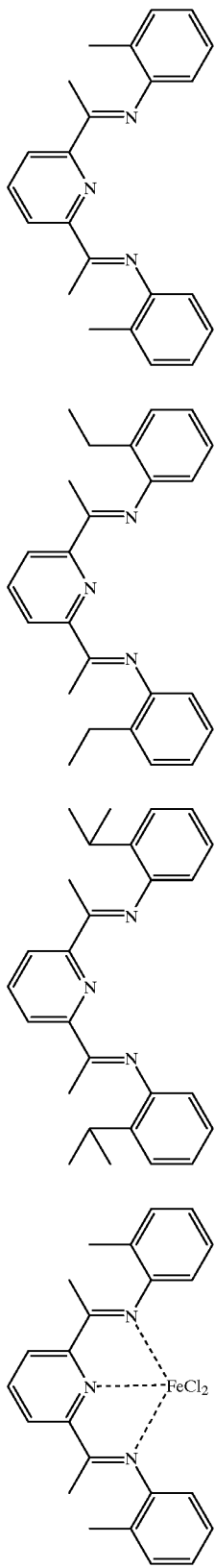

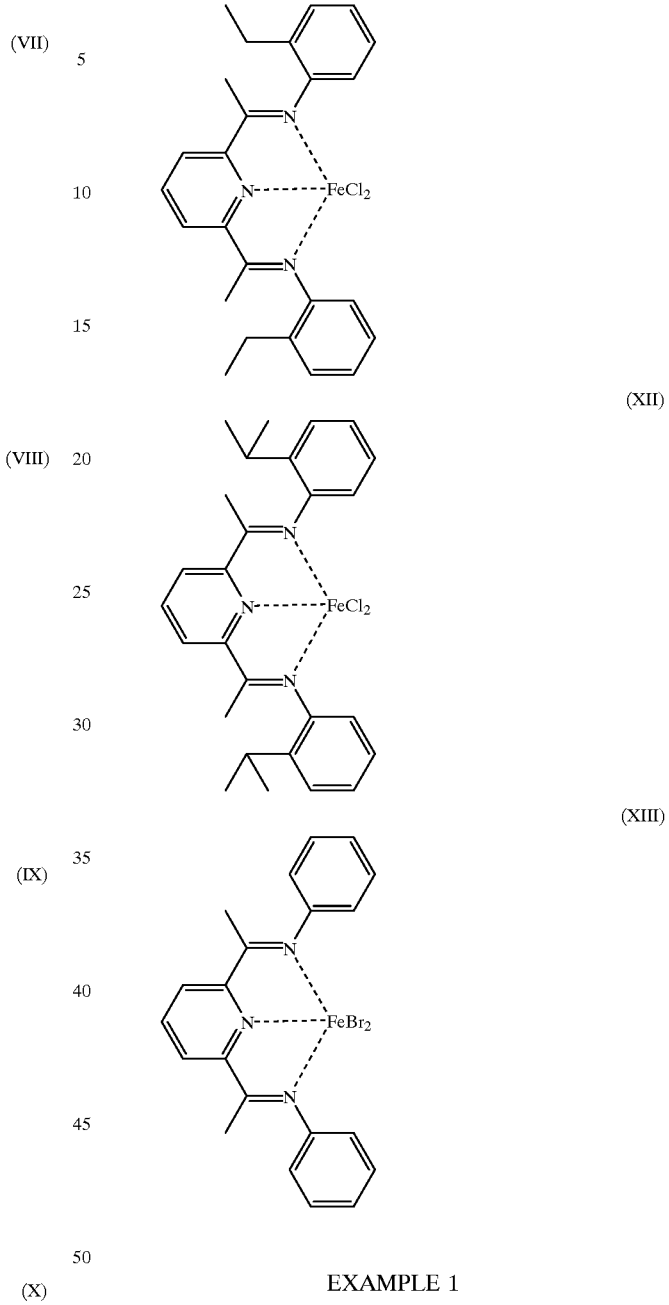

EXAMPLE 1

Preparation of 2,6-bis-[1-(2-methylphenylimino)ethyl]pyridine, (VII)

One g of 2,6-diacetylpyridine and 3.0 ml of o-toluidine were added to an Erlenmeyer flask with 20 ml of methylene chloride. A stirbar and 5 drops of 97% formic acid were added, and the flask was sealed and the solution was stirred for 40 hours. The solvent was then removed in vacuo, and the flask was placed in the freezer at −30° C. The resulting viscous oil was washed with cold methanol, and a yellow solid formed and was isolated by filtration and identified by $^1$H NMR as the desired product (959 mg, 45.9%). $^1$H NMR (CDCl$_3$): δ 8.38(d, 2, H$_{pyr}$), 7.86(t, 1, H$_{pyr}$), 7.20(m, 4, H$_{aryl}$), 7.00(t, 2, H$_{aryl}$), 6.67(d, 2, H$_{aryl}$), 2.32(s, 6, N=C—CH$_3$), 2.10(s, 6, CH$_3$ aryl).

EXAMPLE 2

Preparation of 2,6-bis[1-(2-ethylphenylimino)ethyl] pyridine, (VIII)

One g of 2,6-diacetylpyridine and 3.0 ml of 2-ethylaniline were added to a round-bottom flask with 30 ml of methanol. A stirbar and 5 drops of 97% formic acid were added, and the flask was sealed and the solution was stirred for 24 hours at 50° C. The flask was then cooled to room temperature and placed in a freezer at −30° C. After 1 day, yellow crystals had formed. The crystals were isolated by filtration and identified by $^1$H NMR as the desired product (1.25g, 55.2%). $^1$H NMR (CDCl$_3$): δ 8.38(d, 2, H$_{pyr}$), 7.86(t, 1, H$_{pyr}$), 7.20(m, 4, H$_{aryl}$), 7.07(t, 2, H$_{aryl}$), 6.65(d, 2, H$_{aryl}$), 2.49(q, 4, H$_{benzyl}$), 2.35(s, 6, N—C—$\underline{CH}_3$), 1.14(t, 6, CH$_2\underline{CH}_3$).

EXAMPLE 3

Preparation of 2,6-bis[1-(1-isopropylphenylimino)ethyl] pyridine, (IX)

One g of 2,6-diacetylpyridine and 3.0 ml of 2-isopropylaniline were added to an Erlenmeyer flask with 20 ml of methylene chloride. A stirbar and 5 drops of 97% formic acid were added, and the flask was sealed and the solution was stirred for 40 hours. The solvent was then removed in vacuo, and the flask was placed in the freezer at −30° C. The resulting viscous oil was washed with cold methanol, and a yellow solid formed and was isolated by filtration and identified by $^1$H NMR as the desired product (1.63 g, 66.8%). $^1$H NMR (CDCl$_3$): δ 8.38(d, 2, H$_{pyr}$), 7.32 (d, 2, H$_{aryl}$), 7.18(t, 2, H$_{aryl}$), 7.10(t, 2, H$_{aryl}$), 6.63(d, 2, H$_{aryl}$), 3.00(sept, 2, C$\underline{H}$(CH$_3$)$_2$), 2.37(s, 6, N═C—$\underline{CH}_3$), 1.18(d, 12, CH($\underline{CH}_3$)$_2$).

EXAMPLE 4

Preparation of 2,6-bis-[1-(1-methylphenylimino) ethyl]pyridine Iron[II] Chloride Complex, (X)

(VII) (150 mg, 1.05 eq.) and 84 mg of iron[II] chloride tetrahydrate were added to a Schlenk flask with a stirbar. The flask was back-filled twice with argon, then charged with 15 ml of THF. Stirring was begun and continued for 18 h under static argon pressure, after which the deep blue solid was isolated by filtration and washed with ether and pentane (182 mg, 92%).

EXAMPLE 5

Preparation of 2,6-bis[1-(1-ethylphenylimino)ethyl] pyridine Iron[II] Chloride Complex (XI)

(VIII) (300 mg, 1.05 eq.) and 154 mg of iron[II] chloride tetrahydrate were added to a Schlenk flask with a stirbar. The flask was back-filled twice with argon, then charged with 30 ml of THF. Stirring was begun and continued for 2 h under static argon pressure, after which the deep blue solid was isolated by filtration and washed with ether and pentane (352 mg, 91.7%).

EXAMPLE 6

Preparation of 2,6-bis[1-(1-isopropylphenylimino) ethyl]pyridine Iron[II] Chloride Complex (XII)

(IX) (200 mg, 1.05 eq.) and 95 mg of iron[II] chloride tetrahydrate were added to a Schlenk flask with a stirbar. The flask was back-filled twice with argon, then charged with 15 ml of THF. Stirring was begun and continued for 6 h under static argon pressure, after which the deep blue solid was isolated by filtration and washed with ether and pentane (160 mg, 64.0%).

EXAMPLES 7–23 AND COMPARATIVE EXAMPLE A

In these examples, all pressures are gauge pressures of ethylene.

General procedure for Examples 7, 18 and 19: The iron complex was weighed out and added to a flame-dried 250 ml Schlenk flask with a stirbar. The flask was back-filled at least twice with ethylene, then the flask was charged with the 50 ml toluene. While stirring, 1 ml of modified methylaluminoxane (Akzo Chemical, ~7% by weight of aluminum in heptane) was added via syringe, and the reaction was allowed to run under a constant (atmospheric) pressure of ethylene. The oligomers were isolated by first adding acetone to the oligomerization to destroy any remaining activator and then by removing the solvent in vacuo. The "K" values and purity of the olefins produced was determined by gas chromatography. The "K" value was calculated from the ratio of C$_{16}$/C$_{14}$ compounds in the product mixture.

General procedure for Examples 8–17, 20–23 and Comparative Example A: A 1 L Parr® reactor was heated under vacuum overnight, then back-filled with argon. The reactor was charged with 150 ml of toluene or hexane, and pressurized to 1.4 MPa with ethylene. The reactor was depressurized, and then the iron complex was added (either as a solid or a solution/suspension) together with 50 ml of toluene to the reactor under positive argon pressure. Then modified 1 ml modified methyl aluminoxane solution (as above), was added, and then the reactor was quickly repressurized while stirring the reaction. After depressurizing the reactor, the oligomers were isolated in the same manner described above. Gas chromatography was again used to determine the product purity and "K" values.

Details about these examples and their results are found in Table 1. Reaction conditions given are the ethylene pressure used, temperature, reaction (rxn) time, and the composition and amount of the iron complex. "Solvent" was toluene for all examples, except Examples 20–22 which were done in hexane, and Example 23 which was done in 95:5 (v:v) hexane:1-pentene. Table 1 also lists solid product isolated, the amount of olefin isolated after applying vacuum, and the total yield, which is the total of the solids plus olefin isolated, plus olefin lost during vacuum treatment, as calculated using K, the Schulz-Flory factor. The TOF, the moles of ethylene oligomerized per hour per mole of iron compound, based on the total yield, are also listed, as are the percentages of α-olefin, based on the total amount of olefin present after exposure to vacuum.

TABLE 1

| Ex. No. | Iron Complex | Iron Complex μmole | pressure Mpa | T(° C.) | rxn. time | solids g | isolated g | total g | K | % alpha | TOF |
|---|---|---|---|---|---|---|---|---|---|---|---|
| 7 | (X) | 5.7 | 0.00 | 25 | 3 h | 4.86 | 12.01 | 18.63 | .81 | 84[a] | 48,000 |
| 8 | (X) | 0.13 | 1.4 | 35 | 2 h | 1.5 | 68.1 | 111.5 | .74 | >99[a] | $15.5 \times 10^6$ |
| 9 | (X) | 0.13 | 2.8 | 80 | 2 h | — | 175.0 | 315.6 | .73 | >99[a] | $44.0 \times 10^6$ |
| 10 | (X) | 0.13 | 4.1 | 90 | 30 min. | — | 114.9 | 204.9 | .70 | >99[a] | $114.2 \times 10^6$ |
| 11 | (X) | 0.13 | 2.8 | 90 | 30 min. | — | 74.6 | 136.1 | .70 | >99[a] | $75.8 \times 10^6$ |
| 12 | (X) | 0.13 | 1.4 | 90 | 30 min. | — | 36.3 | 68.4 | .70 | >99[a] | $38.1 \times 10^6$ |
| 13 | (X) | 0.10 | 1.4 | 60 | 30 min. | — | 20.0 | 36.3 | .73 | >99[a] | $25.3 \times 10^6$ |
| 14 | (X) | 0.09 | 2.8 | 60 | 30 min. | — | 53.27 | 94.9 | .73 | >99[a] | $72.1 \times 10^6$ |
| 15 | (X) | 0.09 | 4.1 | 90 | 30 min. | — | 133.4 | 245.3 | .70 | >99[a] | $186.4 \times 10^6$ |
| 16 | (XI) | 0.13 | 1.4 | 60 | 30 min. | 14.1 | 10.7 | 31.3 | .79 | >99 | $17.1 \times 10^6$ |
| 17 | (XI) | 0.11 | 2.8 | 60 | 30 min. | 18.0 | 9.4 | 31.1 | .79 | >99 | $19.7 \times 10^6$ |
| 18 | (XI) | 2.2 | 0.00 | 25 | 1 h | 2.7 | 2.4 | 5.0 | .81 | >98[a] | 81,000 |
| 19 | (XII) | 2.1 | 0.00 | 25 | 1 h | 3.2 | .94 | 4.12 | .87 | >99 | 81,000 |
| 20 | (XI) | 0.036 mg | 1.4 | 50 | 30 min. | — | 17.6 | 24.2 | 0.82 | >99 | $24.1 \times 10^6$ |
| 21 | (XI) | 0.027 mg | 2.8 | 50 | 30 min. | — | 17.6 | 22.4 | 0.82 | >99 | $29.8 \times 10^6$ |
| 22 | (XI) | 0.025 mg | 4.1 | 50 | 30 min. | — | 16.4 | 20.8 | 0.82 | >99 | $29.5 \times 10^6$ |
| 23 | (X) | 0.014 mg | 2.8 | 50 | 30 min. | — | 10.7 | 17.2 | 0.74 | >99 | $39.9 \times 10^6$ |
| A | (XIII) | 2.0 | 1.4 | 30 | 30 min. | — | — | <1.0 g | — | 77.2 | — |

[a]Product mixture contained up to 5 mole percent of branched α-olefins.

What is claimed is:

1. A process for the production of α-olefins, comprising, contacting, at a temperature of about −100° C. to about +300° C., a compound of the formula

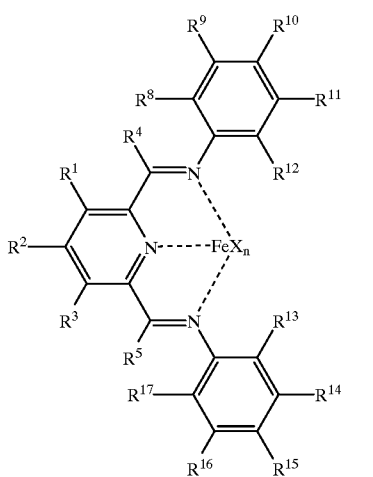

(I)

with ethylene and:
(a) a first compound W, which is a neutral Lewis acid capable of abstracting $X^-$ an alkyl group or a hydride group from Fe to form $WX^-$, $(WR^{20})^-$ or $WH^-$ and which is also capable of transferring an alkyl group or a hydride to Fe, provided that $WX^-$ is a weakly coordinating anion; or
(b) a combination of second compound which is capable of transferring an alkyl or hydride group to Fe and a third compound which is a neutral Lewis acid which is capable of abstracting $X^-$, a hydride or an alkyl group from Fe to form a weakly coordinating anion;

wherein:
each X is an anion;
n is 1, 2 or 3 so that the total number of negative charges on said anion or anions is equal to the oxidation state of an Fe atom present in (I);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^9$, $R^{10}$, $R^{11}$, $R^{14}$, $R^{15}$ and $R^{16}$ are each independently hydrogen, hydrocarbyl, an inert functional group or substituted hydrocarbyl;

$R^8$ is a primary carbon group, a secondary carbon group or a tertiary carbon group; and $R^{20}$ is alkyl;

and provided that:
when $R^8$ is a primary carbon group none, one or two of $R^{12}$, $R^{13}$ and $R^{17}$ are primary carbon groups, and the remainder of $R^{12}$, $R^{13}$ and $R^{17}$ are hydrogen;
when $R^8$ is a secondary carbon group, none or one of $R^{12}$, $R^{13}$ and $R^{17}$ is a primary carbon group or a secondary carbon group and the remainder of $R^{12}$, $R^{13}$, and $R^{17}$ are hydrogen;
when $R^8$ is a tertiary carbon group all of $R^{12}$, $R^{13}$ and $R^{14}$ are hydrogen; and
any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

2. The process as recited in claim 1 wherein:
$R^4$ and $R^5$ are methyl or hydrogen;
$R^1$, $R^2$, and $R^3$ are all hydrogen;
$R^9$, $R^{10}$, $R^{11}$, $R^{12}$, $R^{13}$, $R^{14}$, $R^{15}$ and $R^{16}$ are all hydrogen; and
$R^8$ and $R^{17}$ are each independently methyl, ethyl, propyl or isopropyl.

3. The process as recited in claim 1 wherein:
$R^4$ and $R^5$ are methyl or hydrogen;
$R^{12}$ and $R^{13}$ are hydrogen; and
$R^8$ and $R^{17}$ are each independently methyl, ethyl, propyl or isopropyl.

4. The process as recited in claim 1 wherein:
$R^4$ and $R^5$ are methyl or hydrogen;
$R^{12}$ and $R^{13}$ are hydrogen; and $R^8$ and $R^{17}$ are both methyl.

5. The process as recited in claim 2 wherein $R^8$ and $R^{17}$ are both methyl or ethyl.

6. The process as recited in claim 2 wherein:
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both methyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both ethyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both isopropyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both n-propyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^9$ are both chloro; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both trifluoromethyl.

7. The process as recited in claim 1 wherein said temperature is about 50° C. to about 150° C.

8. The process as recited in claim 1 wherein an ethylene pressure is about 500 kPa to about 15 MPa.

9. The process as recited in claim 1 wherein a factor K is about 0.7 to about 0.8.

10. The process as recited in claim 1 wherein W is an alkyl aluminum compound.

11. The process as recited in claim 10 wherein said alkyl aluminum compound is an alkyl aluminoxane.

12. The process as recited in claim 1 wherein:
if $R^8$ is a primary carbon group, $R^{13}$ is a primary carbon group and $R^{12}$ and $R^{17}$ are hydrogen; or
if $R^8$ is a secondary carbon group, $R^{13}$ is a primary or secondary carbon group, and $R^{12}$ and $R^{17}$ are hydrogen.

13. A process for the production of α-olefins, comprising contacting, at a temperature of about −100° C. to about +300° C., a Fe[II] or Fe[III] complex of a tridentate ligand of the formula

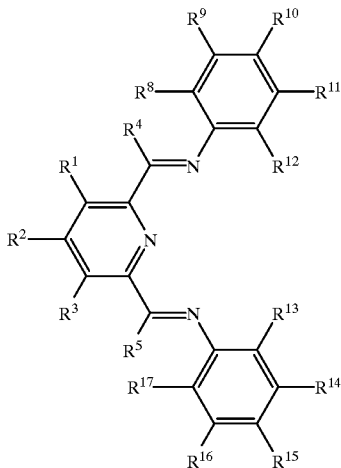

(II)

with ethylene, wherein:
$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;
$R^9, R^{10}, R^{11}, R^{14}, R^{15}$ and $R^{16}$ are each independently hydrogen, hydrocarbyl, an inert functional group or substituted hydrocarbyl;
$R^8$ is a primary carbon group, a secondary carbon group or a tertiary carbon group;

and provided that:
when $R^8$ is a primary carbon group none, one or two of $R^{12}, R^{13}$ and $R^{17}$ are primary carbon groups, and the remainder of $R^{12}, R^{13}$ and $R^{17}$ are hydrogen;
when $R^8$ is a secondary carbon group, none or one of $R^{12}, R^{13}$ and $R^{17}$ is a primary carbon group or a secondary carbon group and the remainder of $R^{12}, R^{13}$, and $R^{17}$ are hydrogen;
when $R^8$ is a tertiary carbon group all of $R^{12}, R^{13}$ and $R^{14}$ are hydrogen;
any two of $R^8, R^9, R^{10}, R^{11}, R^{12}, R^{13}, R^{14}, R^{15}, R^{16}$ and $R^{17}$ vicinal to one another, taken together may form a ring;
an Fe[II] or Fe[III] atom also has bonded to it an empty coordination site or a ligand that may be displaced by said ethylene, and a ligand that may add to said ethylene.

14. The process as recited in claim 13 wherein:
$R^4$ and $R^5$ are methyl or hydrogen;
$R^1$, $R^2$, and $R^3$ are all hydrogen;
$R^9, R^{10}, R^{11}, R^{12}, R^{13}, R^{14}, R^{15}$ and $R^{16}$ are all hydrogen; and
$R^8$ and $R^{17}$ are each independently methyl, ethyl, propyl or isopropyl.

15. The process as recited in claim 13 wherein:
$R^4$ and $R^5$ are methyl or hydrogen; and
$R^8$ and $R^{17}$ are each independently methyl, ethyl, propyl or isopropyl.

16. The process as recifted in claim 13 wherein:
$R^4$ and $R^5$ are methyl or hydrogen; and
$R^8$ and $R^{17}$ are both methyl or ethyl.

17. The process as recited in claim 13 wherein $R^8$ and $R^{17}$ are both methyl or ethyl.

18. The process as recited in claim 13 wherein:
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both methyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both ethyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both isopropyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both n-propyl; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both chloro; or
$R^4$ and $R^5$ are methyl, $R^9, R^{10}, R^{11}, R^{12}, R^{13}, R^{14}, R^{15}$ and $R^{16}$ are all hydrogen, $R^8$ and $R^{17}$ are both trifluoromethyl.

19. The process as recited in claim 13 wherein said temperature is about −50 C. to about 100° C.

20. The process as recited in claim 13 wherein an ethylene pressure is about 500 kPa to about 15 MPa.

21. The process as recited in claim 13 wherein a factor K is about 0.7 to about 0.8.

22. The process as recited in claim 13 wherein:

if $R^8$ is a primary carbon group, $R^{13}$ is a primary carbon group and $R^{12}$ and $R^{17}$ are hydrogen; or if $R^8$ is a secondary carbon group, $R^{13}$ is a primary or secondary carbon group, and $R^{12}$ and $R^{13}$ are hydrogen.

23. A process for the production of α-olefins, comprising, contacting, at a temperature of about −100° C. to about +300° C., ethylene and a compound of the formula

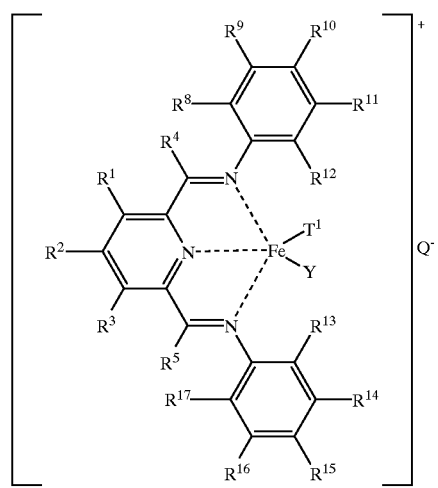

(IV)

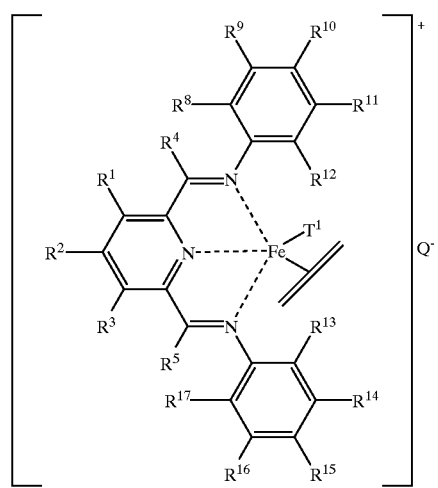

(V)

or

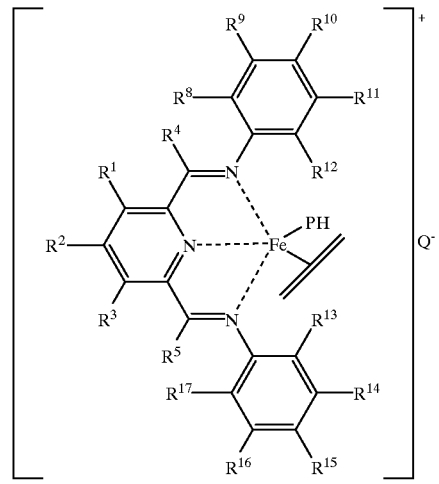

(VI)

wherein:

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl, $R^9$, $R^{10}$, $R^{11}$, $R^{14}$, $R^{15}$ and $R^{16}$ are each independently hydrogen, hydrocarbyl, an inert functional group or substituted hydrocarbyl;

$R^8$ is a primary carbon group, a secondary carbon group or a tertiary carbon group;

$T^1$ is hydride or alkyl or any other anionic ligand into which ethylene can insert;

Y is a vacant coordination site, or a neutral ligand capable of being displaced by ethylene;

Q is a relatively non-coordinating anion; and

P is a divalent (poly)ethylene group of the formula —(CH$_2$CH$_2$)$_x$— wherein x is an integer of 1 or more;

and provided that:

when $R^8$ is a primary carbon group none, one or two of $R^{12}$, $R^{13}$ and $R^{17}$ are primary carbon groups, and the remainder of $R^{12}$, $R^{13}$ and $R^{17}$ are hydrogen;

when $R^8$ is a secondary carbon group, none or one of $R^{12}$, $R^{13}$ and $R^{17}$ is a primary carbon group or a secondary carbon group and the remainder of $R^{12}$, $R^{13}$, and $R^{17}$ are hydrogen;

when $R^8$ is a tertiary carbon group all of $R^{12}$, $R^{13}$ and $R^{14}$ are hydrogen; and any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

24. The process as recited in claim 23 wherein:

$R^4$ and $R^5$ are methyl or hydrogen;

$R^1$, $R^2$, and $R^3$ are all hydrogen;

$R^9$, $P^{10}$, $R^{11}$, $R^{12}$, $R^{13}$, $R^{14}$, $R^{15}$ and $R^{16}$ are all hydrogen; and $R^8$ and $R^{17}$ are each independently methyl, ethyl, propyl or isopropyl.

25. The process as recited in claim 23 wherein:

$R^4$ and $R^5$ are methyl or hydrogen; and $R^8$ and $R^{17}$ are each independently methyl, ethyl, propyl or isopropyl.

26. The process as recited in claim 23 wherein:

$R^4$ and $R^5$ are methyl or hydrogen; and $R^8$ and $R^{17}$ are both methyl or ethyl.

27. The process as recited in claim 23 wherein $R^8$ and $R^{17}$ are both methyl or ethyl.

28. The process as recited in claim 23 wherein:

$R^4$ and $R^5$ are methyl, $R^9$, $R^{10}$, $R^{11}$, $R^{12}$, $R^{13}$, $R^{14}$, $R^{15}$ and $R^{16}$ are all hydrogen, $R^8$ and $R^{17}$ are both methyl; or $R^4$ and $R^5$ are methyl, $R^9$, $R^{10}$, $R^{11}$, $R^{12}$, $R^{13}$, $R^{14}$, $R^{15}$ and $R^{16}$ are all hydrogen, $R^8$ and $R^{17}$ are both ethyl; or $R^4$ and $R^5$ are methyl, $R^9$, $R^{10}$, $R^{11}$, $R^{12}$, $R^{13}$, $R^{14}$, $R^{15}$ and $R^{16}$ are all hydrogen, $R^8$ and $R^{17}$ are both isopropyl; or $R^4$ and $R^5$ are methyl, $R^9$, $R^{10}$, $R^{11}$, $R^{12}$, $R^{13}$, $R^{14}$, $R^{15}$ and $R^{16}$ are all hydrogen, $R^8$ and $R^{17}$ are both n-propyl; or $R^4$ and $R^5$ are methyl, $R^9$, $R^{10}$, $R^{11}$, $R^{12}$, $R^{13}$, $R^{14}$, $R^{15}$ and $R^{16}$ are all hydrogen, $R^8$ and $R^{17}$ are both chloro; or $R^4$ and $R^5$ are methyl, $R^9$, $R^{10}$, $R^{11}$, $R^{12}$, $R^{13}$, $R^{14}$, $R^{15}$ and $R^{16}$ are all hydrogen, $R^8$ and $R^{17}$ are both trifluoromethyl.

29. The process as recited in claim 23 wherein said temperature is about −50° C. to about 100° C.

30. The process as recited in claim 23 wherein an ethylene pressure is about 500 kPa to about 15 MPa.

31. The process as recited in claim 23 wherein a factor K is about 0.7 to about 0.8.

32. The process as recited in claim 23 wherein said compound is (IV).

33. The process as recited in claim 23 wherein said compound (V).

34. The process as recited in claim 23 wherein said compound is (VI).

35. The process as recited in claim 23 wherein:

if $R^8$ is a primary carbon group, $R^{13}$ is a primary carbon group and $R^{12}$ and $R^{17}$ are hydrogen; or if $R^8$ is a secondary carbon group, $R^{13}$ is a primary or secondary carbon group, and $R^{12}$ and $R^{17}$ are hydrogen.

36. The process as recited in claim 1 wherein said compound is or becomes part of a heterogeneous catalyst on a solid support.

37. The process as recited in claim 36 carried out in the gas phase or liquid phase.

38. The process as recited in claim 13 wherein said complex is or becomes part of a heterogeneous catalyst on a solid support.

39. The process as recited in claim 28 carried out in the gas or liquid phase.

40. The process as recited in claim 23 wherein said complex is or becomes part of a heterogeneous catalyst on a solid support.

41. The process as recited in claim 40 carried out in the gas or liquid phase.

* * * * *